(12) United States Patent
Lewis et al.

(10) Patent No.: US 9,949,809 B2
(45) Date of Patent: *Apr. 24, 2018

(54) DENTAL TREATMENT DEVICES COMPRISING SILICONE-LIKE ELASTOMERIC MATERIAL

(71) Applicant: ULTRADENT PRODUCTS, INC., South Jordan, UT (US)

(72) Inventors: Paul E. Lewis, Midvale, UT (US); Scot N. Andersen, Bluffdale, UT (US); Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 359 days.

This patent is subject to a terminal disclaimer.

(21) Appl. No.: 14/303,029

(22) Filed: Jun. 12, 2014

(65) Prior Publication Data

US 2014/0295377 A1    Oct. 2, 2014

Related U.S. Application Data

(60) Continuation of application No. 13/074,485, filed on Mar. 29, 2011, now abandoned, which is a division of
(Continued)

(51) Int. Cl.
*A61C 5/00* (2017.01)
*A61C 19/06* (2006.01)

(52) U.S. Cl.
CPC ............ *A61C 19/066* (2013.01); *A61C 19/06* (2013.01)

(58) Field of Classification Search
CPC ..... A61C 19/06; A61C 19/066; A61C 19/063; A61C 5/00; A61C 5/007; A61C 1/0046
(Continued)

(56) References Cited

U.S. PATENT DOCUMENTS 165,584 A     7/1875    Hopfen
1,637,153 A   7/1927    Lawton
(Continued)

FOREIGN PATENT DOCUMENTS

AT    411146      10/2003
DE    3638888     5/1988
(Continued)

OTHER PUBLICATIONS

GC America, Inc., GC RelineTM Soft/Extra Soft, http://www.gcamerica.com/gcreline.html, Feb. 6, 2002, 2 pgs.
(Continued)

*Primary Examiner* — Cris L Rodriguez
*Assistant Examiner* — Matthew Saunders
(74) *Attorney, Agent, or Firm* — Workman Nydegger

(57) ABSTRACT

Non-customized dental treatment trays used to provide a desired treatment are formed from elastomeric silicone or silicone-like material. They may be molded from a two-part liquid silicone composition or a silicone-like TPE material (e.g., preferably SEBS and/or VERSAFLEX™ thermoplastic elastomer). The dental treatment trays possess high adaptability, flexibility, softness, and elastic elongation while also exhibiting resiliency in order to readily conform to the ridges, depressions and contours of a person's teeth during use. The trays possess a greater ability to adhere to a person's teeth compared to non-elastomeric thermoplastic materials. Due to their high adaptability and conformability, the non-customized dental trays behave like a semi-custom dental tray when placed over conformed to a person's teeth, particularly when used in combination with a sticky, viscous treatment composition.

11 Claims, 5 Drawing Sheets

Related U.S. Application Data application No. 12/183,303, filed on Jul. 31, 2008, now abandoned.

(60) Provisional application No. 61/190,054, filed on Aug. 31, 2007.

(58) Field of Classification Search
 USPC .......................................................... 433/215
 See application file for complete search history.

(56) References Cited

U.S. PATENT DOCUMENTS

| | | | |
|---|---|---|---|
| 1,663,695 A | 3/1928 | Foster, Jr. | |
| 2,257,709 A | 9/1941 | Anderson | |
| 2,833,278 A | 5/1958 | Ross | |
| 2,835,628 A | 5/1958 | Saffir | |
| 2,919,693 A | 1/1960 | Ross | |
| 3,124,129 A | 3/1964 | Grossberg | |
| 3,224,441 A | 12/1965 | Monaghan | |
| 3,247,844 A | 4/1966 | Berghash | |
| 3,312,218 A | 4/1967 | Jacobs et al. | |
| 3,319,626 A | 5/1967 | Lindsay | |
| 3,339,547 A | 9/1967 | Drabkowski | |
| 3,505,995 A | 4/1970 | Greenberg | |
| 3,527,219 A | 9/1970 | Greenberg | |
| 3,577,640 A | 5/1971 | Lee | |
| 3,624,909 A | 12/1971 | Greenberg | |
| 3,625,215 A | 12/1971 | Quisling | |
| 3,688,406 A | 9/1972 | Porter et al. | |
| 3,838,513 A | 10/1974 | Katz et al. | |
| 3,878,610 A | 4/1975 | Coscina | |
| 3,923,754 A | 12/1975 | Pellico | |
| 3,955,281 A | 5/1976 | Weitzman | |
| 4,007,153 A | 2/1977 | Smith | |
| 4,033,774 A | 7/1977 | Johnson et al. | |
| 4,044,762 A | 8/1977 | Jacobs | |
| 4,063,552 A | 12/1977 | Going et al. | |
| 4,064,628 A | 12/1977 | Weitzman | |
| 4,082,693 A | 4/1978 | Kessler et al. | |
| 4,138,814 A | 2/1979 | Weitzman | |
| 4,161,067 A | 7/1979 | Bekey et al. | |
| 4,173,505 A | 11/1979 | Jacobs | |
| 4,361,528 A | 11/1982 | Ginsburg et al. | |
| 4,370,133 A | 1/1983 | Stempel | |
| 4,401,616 A | 8/1983 | Wagner | |
| 4,413,979 A | 11/1983 | Ginsburg et al. | |
| 4,569,342 A | 2/1986 | Von Nostitz | |
| 4,591,341 A | 5/1986 | Andrews | |
| 4,619,610 A | 10/1986 | Pelerin | |
| 4,668,188 A | 5/1987 | Wolfenson et al. | |
| 4,672,081 A | 6/1987 | Fischer et al. | |
| 4,755,139 A | 7/1988 | Abbatte et al. | |
| 4,776,792 A | 10/1988 | Wagner et al. | |
| 4,867,680 A | 9/1989 | Hare et al. | |
| RE33,093 E | 10/1989 | Schiraldi et al. | |
| 4,900,721 A | 2/1990 | Bansemir | |
| 4,902,227 A | 2/1990 | Smith | |
| 4,955,393 A | 9/1990 | Adell | |
| 5,008,093 A | 4/1991 | Merianos | |
| 5,035,613 A | 7/1991 | Breads et al. | |
| 5,051,476 A | 9/1991 | Uji et al. | |
| 5,055,039 A * | 10/1991 | Abbatte | A61C 7/146 433/24 |
| 5,066,231 A | 11/1991 | Oxman et al. | |
| 5,085,585 A | 2/1992 | Zimble | |
| 5,108,742 A | 4/1992 | Merianos | |
| 5,112,225 A | 5/1992 | Diesso | |
| 5,135,392 A | 8/1992 | Polansky | |
| 5,183,901 A | 2/1993 | Login et al. | |
| 5,211,559 A | 5/1993 | Hart et al. | |
| 5,213,498 A | 5/1993 | Pelerin | |
| 5,224,958 A | 7/1993 | Warunek et al. | |
| 5,268,396 A | 12/1993 | Lai | |
| 5,277,202 A | 1/1994 | Hays | |
| 5,277,203 A | 1/1994 | Hays | |
| 5,310,563 A | 5/1994 | Curtis et al. | |
| 5,326,262 A | 7/1994 | Jorgenson | |
| 5,326,685 A | 7/1994 | Gaglio et al. | |
| 5,346,061 A | 9/1994 | Newman et al. | |
| 5,356,291 A | 10/1994 | Darnell | |
| 5,376,006 A | 12/1994 | Fischer | |
| 5,409,631 A | 4/1995 | Fischer | |
| 5,415,544 A | 5/1995 | Oxman et al. | |
| 5,425,953 A | 6/1995 | Sintov et al. | |
| 5,460,527 A | 10/1995 | Kittelsen | |
| 5,462,067 A | 10/1995 | Shapiro | |
| 5,503,552 A | 4/1996 | Diesso | |
| 5,513,988 A | 5/1996 | Jeffer et al. | |
| 5,548,848 A | 8/1996 | Huybrechts | |
| 5,562,449 A | 10/1996 | Jacobs et al. | |
| 5,566,684 A | 10/1996 | Wagner | |
| 5,573,399 A | 11/1996 | McClintock, II | |
| 5,575,654 A | 11/1996 | Fontenot | |
| 5,575,655 A | 11/1996 | Darnell | |
| 5,582,517 A | 12/1996 | Adell | |
| 5,591,786 A | 1/1997 | Oxman et al. | |
| 5,611,687 A | 3/1997 | Wagner | |
| 5,616,027 A | 4/1997 | Jacobs et al. | |
| 5,631,000 A | 5/1997 | Pellico | |
| 5,639,445 A | 6/1997 | Curtis et al. | |
| 5,666,974 A | 9/1997 | Hiro et al. | |
| 5,678,993 A | 10/1997 | Jeffer et al. | |
| 5,702,251 A | 12/1997 | McClintock, II | |
| 5,707,235 A | 1/1998 | Knutson | |
| 5,711,935 A | 1/1998 | Hill et al. | |
| 5,713,738 A | 2/1998 | Yarborough | |
| 5,752,826 A | 5/1998 | Andreiko | |
| 5,769,633 A | 6/1998 | Jacobs et al. | |
| 5,770,182 A | 6/1998 | Fischer | |
| 5,794,627 A | 8/1998 | Frantz | |
| 5,807,100 A | 9/1998 | Thornton | |
| 5,816,802 A | 10/1998 | Montgomery | |
| 5,823,193 A | 10/1998 | Singer et al. | |
| 5,829,441 A | 11/1998 | Kidd et al. | |
| 5,846,058 A | 12/1998 | Fischer | |
| 5,846,082 A | 12/1998 | Thornton | |
| 5,851,512 A | 12/1998 | Fischer | |
| 5,855,870 A | 1/1999 | Fischer | |
| 5,863,202 A | 1/1999 | Fontenot et al. | |
| 5,879,691 A | 3/1999 | Sagel et al. | |
| 5,890,894 A | 4/1999 | Mio et al. | |
| 5,891,453 A | 4/1999 | Sagel et al. | |
| 5,894,017 A | 4/1999 | Sagel et al. | |
| 5,895,218 A | 4/1999 | Quinn et al. | |
| 5,922,307 A | 7/1999 | Montgomery | |
| 5,924,863 A | 7/1999 | Jacobs et al. | |
| 5,947,918 A | 9/1999 | Jones et al. | |
| 5,952,400 A | 9/1999 | Hosoi et al. | |
| 5,980,249 A | 11/1999 | Fontenot | |
| 5,985,249 A | 11/1999 | Fischer | |
| 5,989,569 A | 11/1999 | Dirksing et al. | |
| 5,993,208 A | 11/1999 | Jonjic | |
| 6,012,919 A | 1/2000 | Cross, III et al. | |
| 6,017,217 A | 1/2000 | Wittrock | |
| 6,036,943 A | 3/2000 | Fischer | |
| 6,045,811 A | 4/2000 | Dirksing et al. | |
| 6,080,397 A | 6/2000 | Pfirrmann | |
| 6,089,869 A | 7/2000 | Schwartz | |
| 6,096,328 A * | 8/2000 | Sagel | A61K 8/02 424/401 |
| 6,106,293 A | 8/2000 | Wiesel | |
| 6,126,443 A | 10/2000 | Burgio | |
| 6,136,297 A * | 10/2000 | Sagel | A61K 8/0208 106/35 |
| 6,142,780 A | 11/2000 | Burgio | |
| 6,155,832 A | 12/2000 | Wiesel | |
| 6,183,251 B1 | 2/2001 | Fischer | |
| 6,196,840 B1 | 3/2001 | Zentz et al. | |
| 6,197,331 B1 | 3/2001 | Lerner et al. | |
| 6,244,864 B1 | 6/2001 | Fujiwara et al. | |
| 6,247,930 B1 | 6/2001 | Chiang et al. | |
| 6,251,966 B1 | 6/2001 | Fry et al. | |
| 6,257,239 B1 | 7/2001 | Kittelsen et al. | |

(56) References Cited

U.S. PATENT DOCUMENTS

| | | |
|---|---|---|
| 6,274,122 B1 * | 8/2001 | McLaughlin ........ A61C 19/063 128/860 |
| 6,277,458 B1 | 8/2001 | Dirksing et al. |
| 6,280,196 B1 | 8/2001 | Berghash |
| 6,287,120 B1 | 9/2001 | Wiesel |
| 6,306,370 B1 | 10/2001 | Jensen et al. |
| 6,309,625 B1 | 10/2001 | Jensen et al. |
| 6,312,671 B1 | 11/2001 | Jensen et al. |
| 6,314,960 B1 | 11/2001 | Vines |
| 6,322,360 B1 | 11/2001 | Burgio |
| 6,331,292 B1 | 12/2001 | Montgomery |
| 6,343,932 B1 | 2/2002 | Wiesel |
| 6,354,837 B1 | 3/2002 | Jensen |
| 6,364,665 B1 | 4/2002 | Trettenero |
| 6,379,147 B1 | 4/2002 | Georgakis et al. |
| 6,386,865 B1 | 5/2002 | Suh et al. |
| 6,398,550 B1 | 6/2002 | Caritg |
| 6,409,993 B1 | 6/2002 | Jensen et al. |
| 6,419,903 B1 | 7/2002 | Xu et al. |
| 6,419,906 B1 | 7/2002 | Xu et al. |
| 6,432,188 B1 | 8/2002 | Takai et al. |
| 6,435,873 B1 | 8/2002 | Burgio |
| 6,440,396 B1 | 8/2002 | McLaughlin |
| 6,447,290 B1 | 9/2002 | Williams |
| 6,458,380 B1 | 10/2002 | Leaderman |
| 6,461,158 B1 | 10/2002 | Sagel et al. |
| 6,488,914 B2 | 12/2002 | Montgomery |
| 6,497,575 B2 | 12/2002 | Zavitsanos et al. |
| 6,500,408 B2 | 12/2002 | Chen |
| 6,503,486 B2 | 1/2003 | Xu et al. |
| 6,506,053 B2 | 1/2003 | Wiesel |
| 6,514,483 B2 | 2/2003 | Xu et al. |
| 6,514,484 B2 | 2/2003 | Rajaiah et al. |
| 6,551,579 B2 | 4/2003 | Sagel et al. |
| 6,582,708 B1 | 6/2003 | Sagel et al. |
| 6,607,382 B1 | 8/2003 | Kuo |
| 6,638,496 B2 | 10/2003 | McLaughlin |
| 6,649,147 B1 | 11/2003 | Ye et al. |
| 6,682,721 B2 | 1/2004 | Kim et al. |
| 6,685,923 B2 | 2/2004 | Peterson |
| 6,689,344 B2 | 2/2004 | Chang et al. |
| 6,730,316 B2 | 5/2004 | Chen |
| 6,765,038 B2 | 7/2004 | Mitra |
| 6,780,401 B2 | 8/2004 | Kim et al. |
| 6,840,771 B1 | 1/2005 | Wagner |
| 6,860,736 B2 * | 3/2005 | Allred ....................... A61O 5/00 433/215 |
| 6,884,426 B2 | 4/2005 | Sagel et al. |
| 6,935,857 B1 | 8/2005 | Farrell |
| 6,945,778 B2 | 9/2005 | Jacobs et al. |
| 6,949,240 B2 | 9/2005 | Sagel et al. |
| 6,964,564 B2 | 11/2005 | Phan et al. |
| 6,964,571 B2 | 11/2005 | Andersen et al. |
| 6,981,874 B2 | 1/2006 | Allred et al. |
| 7,004,756 B2 * | 2/2006 | Andersen ................ A61O 5/00 433/215 |
| 7,040,897 B2 | 5/2006 | Fischer et al. |
| 7,048,543 B2 | 5/2006 | Allred et al. |
| 7,052,275 B2 | 5/2006 | Allred et al. |
| 7,056,118 B2 * | 6/2006 | Allred ....................... A61O 5/00 424/53 |
| 7,059,857 B2 * | 6/2006 | Allred ....................... A61O 5/00 424/53 |
| 7,059,858 B2 | 6/2006 | McLean |
| 7,070,413 B1 * | 7/2006 | Wagner ................ A61C 19/066 433/214 |
| 7,074,042 B2 | 7/2006 | Allred et al. |
| 7,094,393 B2 | 8/2006 | Montgomery |
| 7,114,953 B1 * | 10/2006 | Wagner ................ A61C 19/063 433/214 |
| 7,122,199 B2 | 10/2006 | Sagel et al. |
| 7,137,814 B2 | 11/2006 | Fischer |
| 7,172,423 B2 * | 2/2007 | Allred ....................... A61O 5/00 424/53 |
| 7,192,280 B2 * | 3/2007 | Allred ................ A61K 8/0208 424/401 |
| 8,007,277 B2 | 8/2011 | Fischer |
| 8,113,837 B2 * | 2/2012 | Zegarelli ............... A61C 19/063 433/215 |
| 8,202,091 B2 * | 6/2012 | Lewis ................... A61C 19/063 433/215 |
| 8,277,215 B2 | 10/2012 | McLean |
| 8,444,413 B2 | 5/2013 | Fischer |
| 2001/0046654 A1 | 11/2001 | Zavitsanos et al. |
| 2002/0006387 A1 | 1/2002 | Sagel et al. |
| 2002/0006388 A1 | 1/2002 | Sagel et al. |
| 2002/0012685 A1 | 1/2002 | Sagel et al. |
| 2002/0018754 A1 | 2/2002 | Sagel et al. |
| 2002/0081555 A1 | 6/2002 | Wiesel |
| 2002/0146666 A1 | 10/2002 | Sagel et al. |
| 2002/0164292 A1 | 11/2002 | Peterson et al. |
| 2002/0182154 A1 | 12/2002 | McLaughlin |
| 2002/0187111 A1 | 12/2002 | Xu et al. |
| 2002/0187112 A1 | 12/2002 | Xu et al. |
| 2003/0003421 A1 | 1/2003 | Bestenheider et al. |
| 2003/0012747 A1 | 1/2003 | Peterson |
| 2003/0036037 A1 | 2/2003 | Zavitsanos et al. |
| 2003/0044631 A1 | 3/2003 | Sagal et al. |
| 2003/0059381 A1 | 3/2003 | Goodhart et al. |
| 2003/0068284 A1 | 4/2003 | Sagel et al. |
| 2003/0068601 A1 | 4/2003 | Zavitsanos et al. |
| 2003/0082114 A1 | 5/2003 | Kim et al. |
| 2003/0133884 A1 | 7/2003 | Chang et al. |
| 2003/0143407 A1 | 7/2003 | Yamasaki et al. |
| 2003/0194382 A1 | 10/2003 | Chang et al. |
| 2003/0198606 A1 | 10/2003 | Kim et al. |
| 2003/0228264 A1 | 12/2003 | Perna |
| 2004/0002035 A1 | 1/2004 | Jacobs et al. |
| 2004/0005277 A1 * | 1/2004 | Willison ................ A61C 19/06 424/53 |
| 2004/0014006 A1 | 1/2004 | Garrison et al. |
| 2004/0091504 A1 * | 5/2004 | Hamann ............... A61K 8/0208 424/195.17 |
| 2004/0131561 A1 | 7/2004 | McLaughlin |
| 2004/0146837 A1 * | 7/2004 | Andersen ................ A61O 5/00 433/215 |
| 2004/0149292 A1 | 8/2004 | Fujieda et al. |
| 2004/0157192 A1 | 8/2004 | Jacobs et al. |
| 2004/0214140 A1 | 10/2004 | Fischer |
| 2004/0234929 A1 * | 11/2004 | Fischer ..................... A61C 5/00 433/215 |
| 2004/0241615 A1 * | 12/2004 | Allred .................. A61C 19/066 433/215 |
| 2004/0241616 A1 * | 12/2004 | Allred ....................... A61O 5/00 433/215 |
| 2004/0241618 A1 * | 12/2004 | Allred ....................... A61O 5/00 433/215 |
| 2004/0241620 A1 | 12/2004 | Allred |
| 2005/0009972 A1 | 1/2005 | Rauh et al. |
| 2005/0036957 A1 | 2/2005 | Prencipe et al. |
| 2005/0048443 A1 * | 3/2005 | Jacobs .................. A61C 19/063 433/215 |
| 2005/0048444 A1 | 3/2005 | Creamer |
| 2005/0089819 A1 * | 4/2005 | Allred ....................... A61O 5/00 433/215 |
| 2005/0089820 A1 * | 4/2005 | Allred ....................... A61O 5/00 433/215 |
| 2005/0089821 A1 * | 4/2005 | Allred ....................... A61O 5/00 433/215 |
| 2005/0115571 A1 | 6/2005 | Jacobs |
| 2005/0136381 A1 | 6/2005 | Andersen |
| 2005/0186539 A1 * | 8/2005 | McLean ................ A61C 19/066 433/215 |
| 2005/0214720 A1 | 9/2005 | Milanovich et al. |
| 2005/0244793 A1 | 11/2005 | Adell et al. |
| 2005/0249677 A1 * | 11/2005 | Malcmacher ........ A61K 8/0208 424/53 |
| 2005/0256276 A1 | 11/2005 | Elkin et al. |
| 2006/0029908 A1 * | 2/2006 | Allred .................. A61C 19/063 433/215 |
| 2006/0078848 A1 | 4/2006 | Fischer et al. |
| 2006/0084024 A1 | 4/2006 | Farrell |

(56) References Cited

U.S. PATENT DOCUMENTS

| | | | |
|---|---|---|---|
| 2006/0130851 A1 | 6/2006 | Mathias | |
| 2006/0141191 A1* | 6/2006 | Seth | B32B 3/16 428/40.1 |
| 2006/0204455 A1 | 9/2006 | Giniger | |
| 2006/0219250 A1 | 10/2006 | Farrell | |
| 2006/0223033 A1 | 10/2006 | McLean et al. | |
| 2006/0237020 A1 | 10/2006 | Morgan et al. | |
| 2006/0263307 A1* | 11/2006 | Robillard | B32B 15/085 424/53 |
| 2006/0292520 A1* | 12/2006 | Dillon | A61C 19/063 433/80 |
| 2007/0003495 A1 | 1/2007 | Sagel et al. | |
| 2007/0037116 A1 | 2/2007 | Knutson | |
| 2007/0060717 A1* | 3/2007 | Zech | A61K 6/10 525/478 |
| 2007/0166659 A1 | 7/2007 | Haase et al. | |
| 2007/0253990 A1 | 11/2007 | Sagel et al. | |
| 2007/0269471 A1 | 11/2007 | Sagel et al. | |
| 2007/0298380 A1 | 12/2007 | Allred | |
| 2008/0025925 A1 | 1/2008 | Allred | |
| 2008/0050693 A1* | 2/2008 | Fischer | A61C 19/063 433/25 |
| 2008/0187693 A1* | 8/2008 | Nielsen | C08J 7/047 428/34.1 |
| 2008/0295850 A1* | 12/2008 | Lesniak | A61F 5/566 128/862 |
| 2009/0074679 A1 | 3/2009 | Silverman | |
| 2009/0087393 A1* | 4/2009 | Jensen | A61K 8/22 424/52 |
| 2009/0087812 A1 | 4/2009 | Andersen | |
| 2009/0238778 A1 | 9/2009 | Mordas et al. | |
| 2010/0028829 A1* | 2/2010 | Lewis | A61C 19/066 433/80 |
| 2010/0055639 A1* | 3/2010 | Lewis | A61C 19/066 433/39 |
| 2010/0329994 A1* | 12/2010 | Bayerl | A61K 9/0014 424/43 |
| 2011/0171605 A1 | 7/2011 | McLean | |
| 2011/0171606 A1 | 7/2011 | Lewis | |
| 2011/0189637 A1* | 8/2011 | Andersen | A61K 8/33 433/216 |
| 2011/0311938 A1 | 12/2011 | Fischer | |
| 2013/0130194 A1 | 5/2013 | Fischer | |

FOREIGN PATENT DOCUMENTS

| | | |
|---|---|---|
| DE | 4011204 A1 | 10/1990 |
| EP | 0329815 | 8/1989 |
| EP | 1438953 | 7/2004 |
| EP | 1457167 | 9/2004 |
| GB | 2416310 | 2/2006 |
| GR | 1004634 | 7/2004 |
| JP | 61-225105 | 10/1986 |
| JP | 406038988 A | 2/1994 |
| JP | 08/113520 | 7/1996 |
| JP | 2001-70325 | 3/2001 |
| JP | 2002-053418 | 2/2002 |
| JP | 2002-522151 | 7/2002 |
| JP | 2005-058594 | 10/2005 |
| JP | 2006-515790 | 6/2006 |
| JP | 2006-525971 | 11/2006 |
| KR | 20020045224 | 6/2002 |
| WO | WO1988/06869 | 9/1988 |
| WO | WO1991/12777 | 9/1991 |
| WO | WO1993/08761 | 5/1993 |
| WO | WO2002/024100 | 3/2002 |
| WO | WO2003/000216 | 1/2003 |
| WO | WO2003/030851 | 4/2003 |
| WO | WO2005/082266 | 5/2004 |
| WO | WO2004/105629 | 12/2004 |
| WO | WO2004/105683 | 12/2004 |
| WO | WO2005/000147 | 1/2005 |
| WO | WO2006/055910 | 5/2006 |
| WO | WO2009/032453 | 3/2009 |
| WO | WO2009/029886 | 5/2009 |

OTHER PUBLICATIONS

"How Safe is Tooth Bleaching?", www.thefreelibrary.com/How+safe+is+tooth+bleachinq%3F-a0118687915, based on information and belief available at least as early as Nov. 15, 2007.

Hydro-Cast Dental Products, http://www.hydrocast.com/technique/68760.html, Nov. 21, 2001, 3 pgs.

Hydro-Cast Dental Products, Mollosil® Plus, http://www.hydrocast.com/68760.html, Feb. 6, 2002, 2pgs.

Maxxgard, Mouthgard types, http://www.maxxgard.com/mouthguardtypes.html, Feb. 6, 2002, 2 pgs.

Play Safe Sport Brochure, Erkodent, published at least as early as Feb. 6, 2002, 1 pg.

ProTech Permafix, htt://www.dentallabproducts.com/permafix.htm, Nov. 21 2001, 4 pgs.

"RevealSmile", www.reveal.com/services-we-offer/revealsmile, base on information and belief available at least as early as Nov. 15, 2007.

Technical Bulletin: Hydrogen Peroxide-Polyvinylpyrrolidone Polymer Complexes, International Specialty Products, 1361 Alps Road, Wayne, New Jersey 07470, www.ispcorp.com (Dec. 2003).

Types of Athletic Mouthguards, http://www.austindental.com/sports/mouthguards.shtml, Feb. 6, 2002, 4 pgs.

VOCO Scientific Information Denture Relining, Scientific Product Information, http://www.voco.com/usa/ufigelh/wi/wi_ug.htm, Feb. 6, 2002, 13 pgs.

Material Safety Data Sheet—SPI #018460AB, -BD; 01847-AB, -BC Parafilm Grafting Tape; 01851-AB, -CA; 01853-AB, -CA; 01854-AB, -AG Parafilm M Laboratory Sealing Film (http://web.archive.org/web/20030417181801/http://www.2spi.com/catalog/msds/msds01851.html).

U.S. Appl. No. 10/423,242, Dec. 15, 2004, Office Action.
U.S. Appl. No. 10/423,242, May 19, 2005, Office Action.
U.S. Appl. No. 10/446,235, Oct. 4, 2005, Office Action.
U.S. Appl. No. 10/783,597, Apr. 5, 2005, Office Action.
U.S. Appl. No. 10/783,597, Dec. 9, 2005, Notice of Allowance.
U.S. Appl. No. 11/446,924, Dec. 30, 2008, Restriction Requirement.
U.S. Appl. No. 11/446,924, Mar. 30, 2009, Restriction Requirement.
U.S. Appl. No. 11/446,924, Dec. 10, 2009, Office Action.
U.S. Appl. No. 11/446,924, Jul. 2, 2010, Office Action.
U.S. Appl. No. 11/446,924, Sep. 21, 2010, Office Action.
U.S. Appl. No. 11/446,924, Jun. 8, 2011, Office Action.
U.S. Appl. No. 11/446,924, Nov. 21, 2001, Office Action.
U.S. Appl. No. 11/446,924, Feb. 23, 2012, Office Action.
U.S. Appl. No. 11/446,924, Jun. 14, 2012, Notice of Allowance.
U.S. Appl. No. 11/836,664, Jun. 3, 2009, Restriction Requirement.
U.S. Appl. No. 11/836,664, Sep. 25, 2009, Office Action.
U.S. Appl. No. 11/836,664, Mar. 10, 2010, Office Action.
U.S. Appl. No. 11/836,664, Sep. 13, 2010, Office Action.
U.S. Appl. No. 11/836,664, Dec. 27, 2010, Office Action.
U.S. Appl. No. 11/836,664, Apr. 28, 2011, Notice of Allowance.
U.S. Appl. No. 11/865,867, Apr. 6, 2010, Office Action.
U.S. Appl. No. 11/865,867, Aug. 5, 2010, Office Action.
U.S. Appl. No. 11/865,867, Dec. 16, 2010, Office Action.
U.S. Appl. No. 11/865,867, Mar. 5, 2012, Office Action.
U.S. Appl. No. 12/183,303, Sep. 3, 2010, Restriction Requirement.
U.S. Appl. No. 12/183,303, Dec. 10, 2010, Office Action.
U.S. Appl. No. 12/183,303, Sep. 30, 2011, Office Action.
U.S. Appl. No. 12/201,902, Jul. 27, 2010, Office Action.
U.S. Appl. No. 12/201,902, Feb. 4, 2011, Office Action.
U.S. Appl. No. 12/201,902, Jul. 14, 2011, Office Action.
U.S. Appl. No. 12/201,902, Nov. 16, 2011, Office Action.
U.S. Appl. No. 12/201,902, Feb. 23, 2012, Notice of Allowance.
U.S. Appl. No. 13/073,167, Jun. 5, 2012, Office Action.
U.S. Appl. No. 13/073,167, Jan. 18, 2012, Office Action.
U.S. Appl. No. 13/073,167, Jun. 13, 2013, Office Action.
U.S. Appl. No. 13/073,167, Nov. 8, 2013, Office Action.
U.S. Appl. No. 13/073,167, Jan. 28, 2014, Office Action.

(56) References Cited

OTHER PUBLICATIONS

U.S. Appl. No. 13/073,167, May 8, 2014, Office Action.
U.S. Appl. No. 13/073,167, Dec. 12, 2014, Office Action.
U.S. Appl. No. 13/073,167, May 27, 2015, Office Action.
U.S. Appl. No. 13/073,167, Nov. 2, 2015, Office Action.
U.S. Appl. No. 13/073,167, Mar. 30, 2016, Office Action.
U.S. Appl. No. 13/073,167, Jul. 26, 2016, Office Action.
U.S. Appl. No. 13/074,485, Dec. 28, 2011, Office Action.
U.S. Appl. No. 13/074,485, Apr. 23, 2012, Office Action.
U.S. Appl. No. 13/074,485, Mar. 5, 2013, Office Action.
U.S. Appl. No. 13/074,485, Sep. 12, 2013, Office Action.
U.S. Appl. No. 13/074,485, May 9, 2014, Office Action.
U.S. Appl. No. 13/220,346, Jul. 25, 2012, Office Action.
U.S. Appl. No. 13/742,080, Aug. 6, 2013, Office Action.

* cited by examiner

DENTAL TREATMENT DEVICES COMPRISING SILICONE-LIKE ELASTOMERIC MATERIAL

CROSS REFERENCE TO RELATED APPLICATIONS

This application is a continuation of U.S. patent application Ser. No. 13/074,485, filed Mar. 29, 2011, which is a division of U.S. patent application Ser. No. 12/183,303, filed Jul. 31, 2008, which claims the benefit of U.S. Provisional Application No. 61/190,054, filed Aug. 31, 2007. The disclosures of the foregoing applications are incorporated herein in their entirety.

BACKGROUND OF THE INVENTION

1. The Field of the Invention

The present invention is in the field of shaped, flexible dental trays and strips used to deliver a dental bleaching composition to a person's teeth. More particularly, the invention relates to flexible dental trays and strips with enhanced user comfort and tooth adhesion.

2. The Relevant Technology

Virtually all people desire white or whiter teeth. A common bleaching method involves the use of a dental tray that is custom-fitted to a person's teeth and that is therefore relatively comfortable to wear. One type of customized tray is made by vacuum forming a sheet of moisture resistant thermoplastic polymer material over a stone cast of a person's teeth, after which the custom tray may be cut out. Another is customized directly using a person's teeth as a template (e.g., "boil-and-bite" trays). Non-customized trays that approximate the shapes and sizes of a variety of users' dental arches have also been used. A dental bleaching composition is placed into the tray and the tray placed over the person's teeth for a desired period of time.

Another tooth bleaching method involves placing a flexible bleaching strip over a user's tooth surfaces. Conventional bleaching strips comprise a flexible plastic strip coated with a dental bleaching gel of moderate viscosity and relatively low stickiness on the side of the strip facing the user's teeth. To install the bleaching strip, a portion of the bleaching strip is placed over the front surfaces of the user's teeth, and the remainder is folded around the occlusal edges of the teeth and against a portion of the lingual surfaces.

Because of the generally poor adhesion of bleaching strips to the user's teeth, coupled with their generally flimsy nature, it is often difficult for the user to maintain the bleaching strip in its proper position for the recommended time. Conventional bleaching strips are prone to slip off the teeth as a result of even minimal movement of the user's mouth, jaw or tongue. It is recommended that the user not eat, drink, smoke or sleep while wearing the bleaching strip. In some cases, the bleaching strip can become so dislodged or mangled that it must be removed by the user and replaced with a fresh bleaching strip to complete the recommended bleaching time.

Ultimately, the main impediment to successful bleaching is the failure of users to complete the prescribed bleaching regimen. If the bleaching apparatus is difficult to install over a person's teeth, requires numerous repetitions to achieve observable results, and/or is uncomfortable to wear, the user may simply give up and prematurely abort the prescribed bleaching regimen. Thus, even if dental bleaching is possible using a particular bleaching apparatus or method, it is less likely to occur if the inadequacies of the bleaching apparatus or method cause a user to become discouraged before desired results are attained.

BRIEF SUMMARY OF THE PREFERRED EMBODIMENTS

The present invention generally relates to improved dental treatment trays and strips used to deliver a dental treatment composition (e.g., a dental bleaching composition) to a person's teeth. The inventive dental treatment trays and strips are formed from silicone or a material which exhibits properties similar to silicone (e.g., styrene-ethylene-butylene-styrene (SEBS), and/or VERSAFLEX™, a proprietary thermoplastic elastomer alloy exhibiting elasticity and other properties similar to silicone. VERSAFLEX™ is sold by GLS Corporation, based in McHenry, Ill.). SEBS and VERSAFLEX™ are thermoplastic elastomers and may hereafter be referred to as "silicone like materials". These materials exhibit excellent adaptability, flexibility, elasticity, and softness, while also exhibiting resiliency (i.e., the ability to spring back once a force is released). Such a combination of properties translates into enhanced comfort during use by the user. Because trays formed of silicone or silicone like materials exhibit such beneficial characteristics even with relatively thick wall thicknesses, they have an added advantage of reduced flimsiness, making them easier to place. In other words, a silicone or silicone like dental treatment tray having a given wall thickness will exhibit adaptability, flexibility, and softness that is at least as good, and typically significantly greater than, a thinner tray formed of more common thermoplastic materials (e.g., EVA). In addition, the silicone tray will exhibit elasticity and excellent resiliency, which the more common thermoplastic polymer materials tend to lack.

Silicone is both more comfortable and more adhesive to teeth and surrounding oral tissues. Thus, it can be both more flexible compared to conventional tray and strip materials while more reliably remaining in place over a person's teeth. Conventional strips are notoriously non-adhesive to teeth and readily slip off and/or become mangled in short order. Silicone is also more resilient than conventional tray and strip materials notwithstanding its also more flexible and comfortable, which further helps it maintain itself in the correct orientation over a person's teeth.

Such silicone and silicone like trays and strips even have improved characteristics relative to trays and strips made from thermoplastic materials which also include a significant fraction of one or more plasticizers (e.g., mineral oil, paraffin oil, paraffin wax, petrolatum, liquid petrolatum, and/or nujol), which is really an attempt to mimic silicone like qualities with more common thermoplastic polymer materials. Although silicone raw materials may be significantly more expensive than the commonly thermoplastic polymer materials (e.g., EVA, PCL, PVC, PP, PE, polyesters, polycarbonates, polyamides, polyurethanes, and polyesteramides), the inventors' practical experience has shown that labor costs in manufacturing relatively comfortable thin wall (e.g., less than about 0.4 mm) dental treatment trays from plasticized thermoplastic materials are so significant, that a cost savings and improved tray characteristics may be realized by forming the trays from silicone or a silicone like material instead. Similar advantages are associated with strips formed of silicone.

When using silicone, it is not necessary to mix the forming material with other components. According to one such embodiment, the dental tray is formed of a material consisting essentially or even solely of silicone. The ability to eliminate the need for additional materials greatly simplifies manufacture, as only the silicone material (e.g., provided as a medical grade thermoset two-part liquid composition) is needed.

As SEBS and VERSAFLEX™ are thermoplastic materials, it may be easier to mix additional components with these materials so that the dental tray is formed of SEBS and/or VERSAFLEX™, although any such additional materials are preferably included in small amounts (e.g., no more than about 10% by weight, more preferably not more than 5% by weight, more preferably not more than 3% by weight, even more preferably not more than 1% by weight), as the best results have been found when the forming material consists essentially of silicone or a silicone like material.

The silicone dental trays and strips are characterized by wall thicknesses of no more than about 1 mm, typically between about 0.03 mm and about 1 mm, more typically between about 0.1 mm and about 0.5 mm. Wall thicknesses greater than about 1 mm have little or no use as a comfortable dental tray or strip, as the thickness of the tray or strip begins to interfere with the normal relaxed position of the occlusal tooth surfaces when wearing such a tray or strip, and otherwise making the tray or strip significantly less comfortable than a tray or strip with a wall thickness that is no more than about 1 mm. For example the tray(s) get in the way between oppositely disposed teeth, preventing the user from completely closing their jaw, and the overall bulk of the tray becomes very noticeable and uncomfortable within the user's mouth.

The durometer hardness/softness of the silicone or silicone like material is selected so as to strike a balance between softness and wall thickness. Within the preferred wall thicknesses described above (i.e., about 0.03 mm to about 1 mm) the shore A durometer hardness value will preferably range from about 90 to about 20. Generally, higher durometer values (less softness) are preferred with thinner wall trays, while lower durometer values (greater softness) are preferred with thicker wall trays. For example, a tray with a wall thickness of about 0.25 mm may advantageously have a shore A durometer hardness value of about 40, while a tray with a wall thickness of about 0.1 mm may have a shore A durometer hardness value of about 70.

In one example, the treatment tray is configured so as to include a buccal-labial side wall (i.e., a front side wall) and a bottom wall adjacent the buccal-labial wall so as to have an approximately L-shaped cross section. Alternatively, the tray may also include a lingual side wall (i.e., a rear side wall) which extends laterally from an opposite side of the bottom wall such that the tray has an approximately U-shaped cross section.

The dental treatment trays may be either custom or non-custom. In other words, silicone or a silicone like material may be used to form a custom dental tray designed to fit the unique size, shape, and overall dentition of an individual's upper or lower dental arch. Typically a pair of trays is custom formed, one for the upper dental arch and one for the lower dental arch. Such trays may typically be formed over a stone cast representing the unique dental arch of a single user. As SEBS and VERSAFLEX™ are thermoplastic materials, they may be preferred materials for use in forming a custom dental tray, as they may be thermoformed over a stone cast.

In the case of a non-custom dental tray, the tray is pre-formed during manufacture so as to be substantially devoid of structures corresponding to the size and shape of a person's unique dentition so that the tray is designed to comfortably fit over a plurality of differently-sized and/or shaped teeth corresponding to different people. Such a non-custom tray may be pre-loaded with a dental treatment composition. The treatment composition may comprise a sticky viscous gel, a less viscous gel, a highly viscous putty, or a substantially solid composition that is less adhesive prior to being moistened with saliva or water but that becomes more sticky and adhesive when moistened.

The size and shape of such non-custom trays (or non-custom strips) according to the invention can be tailored to readily fit a person's upper or lower dental arch. The treatment trays and strips may come in various sizes (e.g., small, medium and large) to better adapt to differently-sized dental arches and/or teeth among the population at large. The dental treatment trays and strips are advantageously designed so as to substantially cover the front and lingual surfaces of the teeth and/or gums to be treated.

According to one embodiment, relatively thin dental treatment trays or strips (e.g., having wall thicknesses less than about 0.4 mm) may be used in combination with a supporting structure, such as an outer support tray, prior to use. An outer support tray is particularly useful when the dental tray or strip is so thin and flexible (i.e., somewhat flimsy) as to be difficult to place over a person's teeth without the side wall(s) collapsing inwardly. As described above, the durometer hardness of the silicone or silicone like material will preferably be somewhat higher with such thin-wall trays and strips in order to reduce their tendency to collapse inwardly. The outer support tray may have the same configuration as the treatment tray so as to receive and support the treatment tray in a nesting fashion. In one embodiment, the outer support tray includes a handle to facilitate gripping and maneuverability of the outer support tray while placing the treatment tray over the teeth. Once positioned, the outer support tray can be removed so as to leave the treatment tray in place over the teeth.

Of course, silicone or silicone like dental trays and strips may advantageously be formed with sufficient wall thickness (e.g., at least about 0.45 mm) so that they exhibit sufficient self-supporting integrity (i.e., they are not so flimsy that the side wall(s) collapse inwardly) so that no outer support tray or other supporting structure is required. Such relatively thick trays advantageously exhibit excellent adaptability, resiliency, softness, flexibility, and comfort which is greater than a similarly sized tray formed of, for example an EVA/PP and plasticizer blend.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

The present invention relates to silicone or silicone like dental treatment trays and strips used to deliver a dental treatment composition to a person's teeth. Surprisingly, forming the trays and strips from silicone or a silicone like material is able to provide both better adaptability (i.e., the ability of a non-custom tray to be shaped and adapted to conform to the user's dental arch) as compared to more commonly used materials (e.g., EVA), while also providing increased resiliency (i.e., the ability of the tray structure to spring back into place), which unique combination of properties (adaptability and resiliency) is counterintuitive and surprising. Because trays and strips formed of silicone or a silicone like material exhibit such characteristics even with relatively thick wall thicknesses (e.g., between about 0.45 mm and about 1 mm), when formed with such thicknesses, they have an added advantage of reduced flimsiness, making them easier to place (i.e., no outer support tray is required). In other words, a silicone or silicone like dental treatment tray or strip having a given wall thickness will exhibit adaptability, flexibility, and softness that is at least as good, and typically significantly greater than, a thinner tray or strip formed of more common thermoplastic materials (e.g., EVA). In addition, the silicone or silicone like dental tray or strip exhibits excellent resiliency and elasticity, which qualities are often lacking in trays and strips formed of other materials. The unique combination of properties increases the comfort to the user, which might be expected to increase compliance with a given treatment regimen.

II. Exemplary Silicone or Silicone Like Dental Trays

Figure 1:
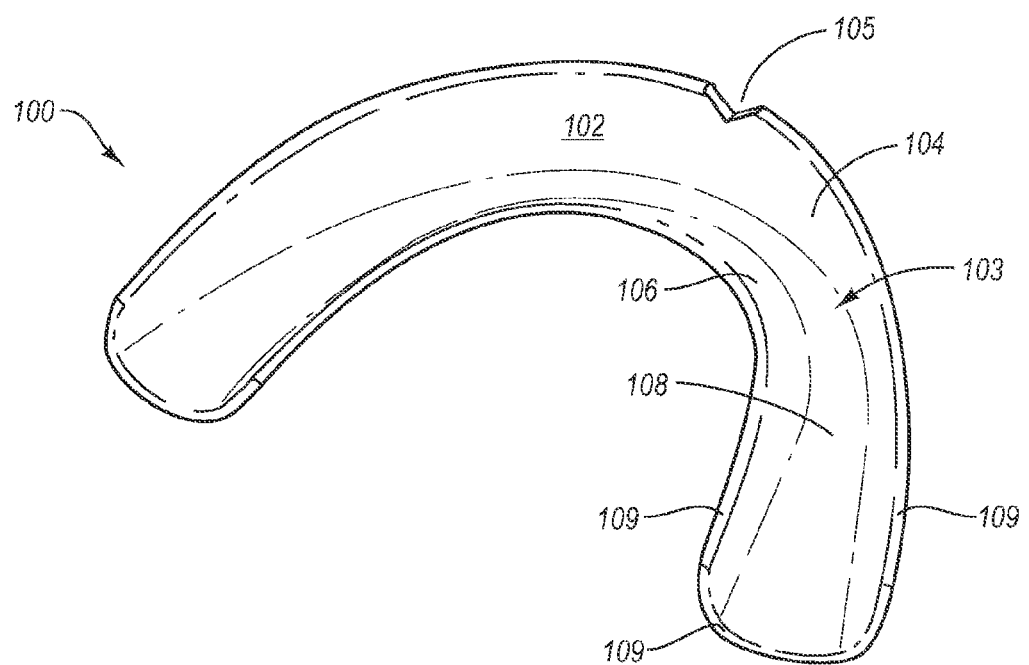
FIG. 1 is a perspective view of an exemplary non-custom dental treatment tray according to the invention.

FIG. 1 illustrates an exemplary non-custom dental tray 100 which is formed by liquid injection molding a silicone or silicone like material. For example, a silicone material may initially comprise a two-part composition including a first part comprising one or more siloxanes and a second part including an activator. Upon mixing the two liquid parts together, the siloxane(s) polymerizes and cross-links so as to form a polysiloxane. Heat may be applied (e.g., by heating the mold) to accelerate polymerization of the silicone material. For example, part A and part B of the raw silicone material are mixed together, which causes the silicone to begin to polymerize. For many exemplary silicone materials, this reaction could take 2-6 weeks to completely cure at room temperature. Heating the mixture significantly increases the rate at which the material polymerizes. For example, according to one method, the material is heated to 375° F. so as to cause the material to polymerize in a matter of seconds. Actual polymerization time depends on the thickness of the tray or strip being formed. The inventive trays and/or strips may also be formed by other methods, for example in which a two part silicone in which polymerization is activated by mixing and/or by compression.

Dental treatment tray 100 includes a shaped tray body 102. The shaped tray body 102 includes a buccal-labial front side wall 104, a lingual rear side wall 106, and a bottom wall 108 bridging the buccal-labial wall 104 and buccal-labial wall 106. Bottom wall 108 is adjacent to buccal-labial wall 104 such that buccal-labial wall 104 extends laterally from bottom wall 108 in a substantially vertical direction. Buccal-labial wall 104 is shown as including an optional v-shaped cut 105 formed along the top surface thereof, near the center where the incisors reside during use. Such a cut helps wall 104 to stretch and flex so as to better accommodate the incisors. Although not shown, such a similar cut or discontinuity may be formed within lingual wall 106. Lingual wall 106 is disposed at the opposite side of bottom wall 108, extending laterally upwardly and outwardly therefrom. The buccal-labial wall 104, lingual wall 106, and bottom wall 108 together form a shaped tray body 102 having an approximate U-shaped cross section and a generally horseshoe-shaped curvature.

The size, shape and curvature of the shaped tray body 102 are advantageously selected in order for the horseshoe-shaped curvature to generally approximate the curvature of a person's dental arch. The U-shaped cross section generally corresponds to and defines an interior cavity of the tray body 102. The depth of the interior cavity is selected in order for the buccal-labial and lingual walls 104 and 106 respectively to extend over a desired portion of a person's teeth, and optionally, over a portion of the person's gums. Because of the excellent adaptability, flexibility, elasticity, and resiliency afforded by the silicone or silicone like material from which shaped tray body 102 is formed, the ability of buccal-labial wall 104, lingual wall 106, and bottom wall 108 to conform and adapt to a person's teeth is increased relative to trays formed of other materials.

Because of its non-custom nature (i.e., tray shaped body 102 is substantially devoid of structures corresponding to the size and shape of a person's unique dentition), the tray shaped barrier layer body 102 comfortably fits over a plurality of differently sized and/or shaped teeth corresponding to different people. Nevertheless, it is within the scope of the invention to provide separate dental trays that are sized and configured to correspond to either a person's upper or lower dental arch, as the lower dental arch is typically smaller than the upper arch, with lower teeth that are typically smaller than the upper teeth. It is also within the scope of the invention to provide varyingly-sized bleaching trays to account for variability among different people's dental arches and/or teeth (e.g., adults versus children, larger mouths versus average or smaller mouths, and larger teeth versus average or smaller teeth).

The tray body 102 may be injection molded, vacuum formed, cut and/or stamped from a sheet of polymeric material, although injection molding is preferred over methods that involve cutting and/or stamping because the outer edges 109 of each wall may be injection molded so as to have a smooth, rounded edge surface as opposed to the sharp, angled surfaces formed when a tray is cut or stamped from a sheet of material. Such smooth edges also contribute to the overall comfortable feel of the tray.

Tray 100 includes an inner treatment surface 103 that includes the inwardly oriented surfaces of buccal-labial front side wall 104, bottom wall 108, and lingual rear side wall

106 that will be positioned against tooth tissue to be bleached during use. At least a portion of inner surface 103 may include one or more bleaching agent destabilizers. In one embodiment, the destabilizer may be compounded with the moisture resistant (e.g., polymeric) material from which the tray 100 is formed. In such an example, the destabilizer is distributed substantially evenly throughout the material from which tray 100 is formed, so that at least some destabilizer is present on inner treatment surface 103. In another embodiment, the destabilizer may be applied to at least a portion of inner surface 103, for example, by spraying, brushing, or otherwise applying the destabilizer onto the inner treatment surface 103. Advantageously, the destabilizer may be present on at least that portion of inner surface 103 corresponding to surfaces of the teeth to be bleached. For example, the destabilizer may be present on at least the lower portion of buccal-labial front side wall 104 nearest bottom wall 108, which corresponds to the labial surface of the teeth to be bleached. Destabilizers may advantageously be absent from any portions of the tray designed to contact gingival tissue, where no bleaching is to take place.

The one or more bleaching agent destabilizers act to destabilize the peroxide dental bleaching agent during use. When peroxides are destabilized they more rapidly release free radicals, which cause tooth bleaching. For example, it is believed that peroxide dental bleaching agents are destabilized to form predominantly hydroxyl (HO.) free radicals, although peroxyl (.OOH), super oxide (.O), and super dioxide (.OO) free radicals may also be formed. Upon decomposition, which is accelerated by the bleaching agent destabilizer, these free radicals are more easily able to pass into the tooth enamel to the location of tooth stains as compared to the larger peroxide ($H_2O_2$) molecules, which may have increased difficulty passing through tight spaces of the enamel to stain locations because of their larger size. The bleaching agent destabilizer is advantageously retained on at least inner treatment surface 103 of the tray or strip prior to use, and upon contact with a peroxide dental bleaching agent in the presence of water; the destabilizer becomes activated, resulting in formation of free radicals from the peroxide for increased bleaching effect.

One class of bleaching agent destabilizers includes transition and/or alkaline earth metal ions. Non-limiting examples of suitable metal ions include magnesium ions, iron ions, titanium ions, cobalt ions, nickel ions, copper ions, platinum ions, tin ions, zinc ions, manganese ions, chromium ions, silver ions, aluminum ions, and combinations thereof. Magnesium and/or iron ions are particularly preferred. Another class of bleaching agent destabilizer includes enzymes, particularly organo-metallic enzymes containing transition metals, such as iron. Examples include "peroxidase" and "catalase", which is described more particularly in U.S. Pat. No. 6,485,709 to Banerjee et al., herein incorporated by reference with respect to its disclosure of organo-metallic enzymes.

One or more bleaching agent destabilizers including the above metal ions in available form and/or organo-metallic enzymes are preferably collectively included in an amount in a range of about 0.01% to about 20% by weight of the polymeric material, more preferably in a range of about 0.05% to about 10% by weight, and most preferably about 0.1% to about 5% by weight. Examples of suitable metal compounds include iodides, nitrates, chlorates, borates, perchlorates, and perborates of suitable metal cations. Preferred specific compounds include MgO, ferric sulfate, ferric chloride, $MnO_2$, and $TiO_2$. Less preferred bleaching agent destabilizers include elemental metals (e.g., iron, silver, platinum, copper, magnesium, titanium, cobalt, nickel, tin, zinc, chromium, aluminum, and/or manganese in powder form). Of course, any other metal ions mentioned herein may also be used in elemental form. Another class of bleaching agent destabilizers that may be used include iodine salts (e.g., potassium iodide and/or sodium iodide).

Many of the metal ion containing compounds are believed to react with the peroxide bleaching agent according to Fenton's Reaction, for example, ferric $Fe^{2+}$ ions react to form ferrous $Fe^{3+}$ ions in the presence of peroxide, releasing oxygen free radicals. During the course of the reaction, the peroxide is regenerated, allowing more ferric ions to react, resulting in production of more oxygen free radicals.

Figure 2A:
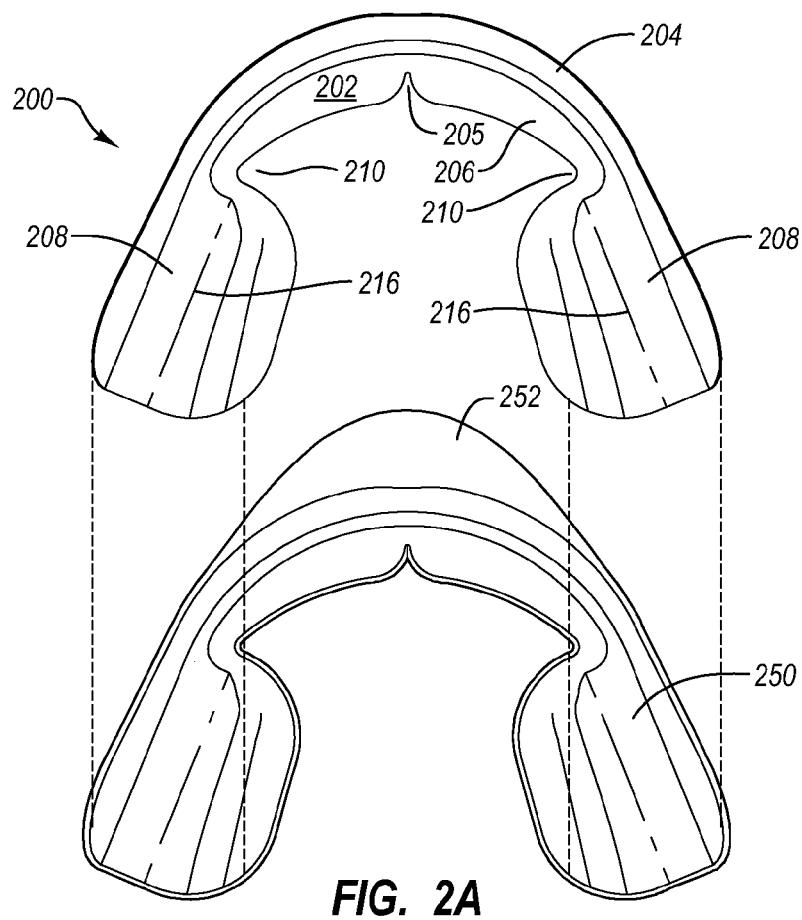
FIG. 2A is an exploded view of a dental treatment tray having anatomical features to improve fit and an optional complementary outer support tray.

FIG. 2A illustrates an alternative non-custom dental treatment tray 200 including a shaped tray body 202 that may be liquid injection molded from a two-part silicone material or injection molded from a silicone like TPE material. The adaptability and elasticity of the silicone or silicone like material allows such a non-custom tray to more closely conform and adapt to the person's dental arch, with excellent comfort. Tray 200 includes anatomical structural features that allow tray 200 to more closely conform to a person's teeth during use. Body 202 includes a buccal-labial front side wall 204, a bottom wall 208, and a lingual side wall 206 connected to bottom wall 208 at an opposite side relative to buccal-labial wall 204. An inner treatment surface 203 is defined by interior portions of bottom wall 208, buccal-labial front side wall 204, and lingual side wall 206. Illustrated tray 200 is sized and configured for placement over a person's upper dental arch. As illustrated, lingual wall 206 may advantageously include a notch 205, which allows the non-custom tray 200 to more easily spread open or compress in the area of the incisors. This is helpful in allowing the lingual wall 206 of the non-custom tray 200 to more easily conform to differently-sized dental arches. Bottom wall 204 includes an abrupt reduction in width positioned at locations 210 corresponding to a transition between posterior teeth (i.e., bicuspids and molars) and anterior teeth (i.e., canines and incisors). Bottom wall 208 also advantageously includes two v-shaped indentations 216 for insertion into the depression between the occlusal peaks of the posterior teeth (i.e., the bicuspids and molars).

Similar to tray 100, at least a portion of inner surface 203 of tray 200 may include one or more bleaching agent destabilizers. In a preferred example, the one or more dental bleaching agent destabilizers may be compounded with the moisture resistant polymeric material from which the tray 200 is formed. In such an example, the destabilizers may be distributed substantially evenly throughout the material from which tray 200 is formed, so that at least some destabilizer is present on inner treatment surface 203. Alternatively, one or more bleaching agent destabilizers may be applied (e.g., after molding or otherwise forming tray body 202) to at least a portion of inner treatment surface 203 where dental bleaching composition will be applied during use, and which surfaces of the tray will be placed against tooth tissues to be bleached during use.

Figure 2B:
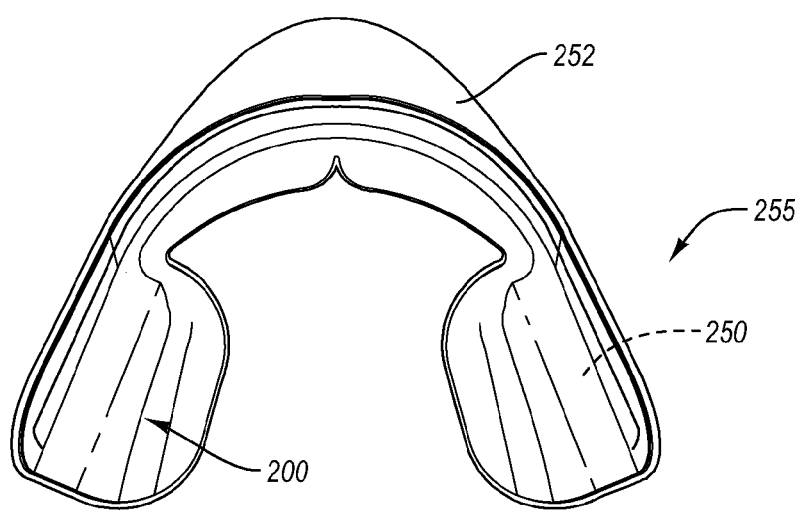
FIG. 2B is a perspective view showing the dental treatment tray nested within the outer support tray.

FIG. 2A is an exploded view showing the dental treatment tray 200 in combination with a corresponding optional outer support tray 250 that is complementarily shaped so as to be capable of receiving the dental treatment tray 200 in a nested configuration (see FIG. 2B). The outer support tray 250 may include the same anatomical features as tray 200 in order to provide a closer fit. The outer support tray 250 advantageously includes a handle 252 extending outwardly from a central portion of the buccal-labial front wall in order to facilitate gripping by the user during placement of the dental bleaching tray 200 over the person's teeth.

In FIG. 2B, dental treatment tray 200 is nested within outer support tray 250 so as to form a dental tray assembly 255. The handle 252 extends beyond the buccal-labial wall of tray 200 in order to facilitate placement and removal of the outer support tray 250 after placement of tray 200 over the person's teeth.

Figure 3:
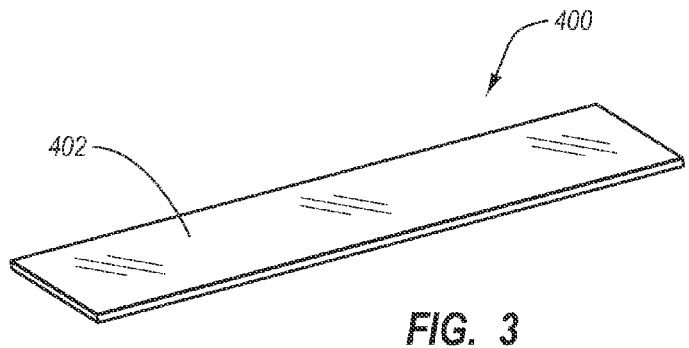
FIG. 3 is a perspective view of an exemplary dental treatment strip according to the present invention.

FIG. 3 illustrates an exemplary dental treatment strip 400 which is formed from a polymeric material. Strip 400 is advantageously formed from silicone or a silicone like material. Silicone is both more comfortable and more adhesive to teeth and surrounding oral tissues as compared to materials currently used to manufacture dental strips (e.g., EVA). Thus, it can be both more flexible compared to conventional strip materials while more reliably remaining in place over a person's teeth. Conventional strips are notoriously non-adhesive to teeth and readily slip off and/or become mangled in short order. As such, strips formed of silicone or a silicone like material provide both better adaptability (i.e., the ability of a non-custom strip to be shaped and adapted to conform to the user's dental arch) as compared to more commonly used materials (e.g., EVA), while also providing increased adhesiveness (i.e., the ability of the strip material itself to grip or adhere to tooth tissue). Strips are generally formed so as to be relatively thin (e.g., between about 0.03 mm and about 1 mm, more typically between about 0.1 and about 0.5 mm).

The inventors have found that given these thicknesses and the strip's shape, the resilient nature of the silicone (which is advantageous in tray structures) is overshadowed by the adhesive, gripping characteristics of the material. In other words, relatively thin strips of silicone do not exhibit shape memory resiliency to a degree that might otherwise cause the silicone strip to not adhere to the tooth surfaces once folded over. Rather, the adhesive, gripping characteristics of the silicone material, in addition to the adhesiveness of the bleaching composition, hold the strip in place. This adhesive, gripping characteristic (which appears to be a surface phenomenon of the material) is also present in trays formed of silicone and silicone like materials, which helps the material grip and adhere to tooth tissue Dental treatment strip 400 is initially substantially rectangular and includes a planar surface 402 which can be positioned adjacent the teeth to be bleached and folded along the incisal edge of the teeth so as to cover the labial and incisal tooth surfaces. Depending on the position of the fold during placement, a portion (or substantially all) of the lingual tooth surfaces may also be covered by the strip 400 once placed. At least a portion of planar surface 402 defines an inner treatment surface corresponding to portions of surface 402 which are positioned adjacent to particularly the labial teeth surfaces during use.

At least a portion of inner planar surface 402 oriented toward a person's tooth surfaces may include one or more bleaching agent destabilizers. In a preferred example, the one or more dental bleaching agent destabilizers may be compounded with the moisture resistant polymeric material from which the strip 400 is formed. In such an example, the destabilizers may be distributed substantially evenly throughout the material from which strip 400 is formed, so that at least some destabilizer is present on planar treatment surface 402. Alternatively, one or more bleaching agent destabilizers may be applied (e.g., after forming of strip barrier layer 400) to at least a portion of inner treatment planar surface 402 where dental bleaching composition will be applied during use and which surfaces of the strip will be placed against tooth tissues to be bleached during use.

Although conventional strips are less effective in treating teeth relative to tray shaped barrier layers because strips tend to readily slip off and/or become mangled before treatment is complete, an improved dental treatment strip can be provided according to the present invention by providing a bleaching agent destabilizer compounded within or otherwise disposed on an inner treatment surface of the strip. Such strips may provide for improved bleaching as the destabilizer acts to promote formation of active bleaching free radicals from the peroxide bleaching agent, which may be expected to result in faster bleaching, at least partially counteracting the disadvantages (i.e., tendency to slip off and/or mangle) of strips.

Any silicone or silicone like dental tray or strip according to the invention may be provided separately from a dental treatment composition, which is introduced into the tray (e.g., adjacent the tray's inner treatment surface) or applied onto the strip by the user immediately prior to use. In one alternative embodiment, it may be possible to prefill a tray or preapply a dental bleaching composition to a strip if the bleaching composition is anhydrous. The anhydrous dental bleaching composition may be disposed directly in contact with the barrier layer, and will not react prematurely because of the anhydrous nature of the bleaching composition. As soon as water is added to the system (e.g., when contacted by saliva by placing the pre-filled tray or pre-applied strip on the teeth), reaction between the destabilizer and bleaching agent will begin. Embodiments including an anhydrous dental bleaching composition may advantageously be sealed within a protective package to prevent absorption of water from the surrounding air during shipment and storage.

Another alternative embodiment may include an anhydrous adhesive composition (e.g., including polyvinyl pyrollidone as an adhesive agent) that also includes a bleaching agent destabilizer (e.g., potassium iodide). The adhesive destabilizing composition may be coated over the barrier layer (e.g., as a thin layer or film). It is important to note that such a composition including the bleaching agent destabilizer is applied to a region of the barrier layer corresponding to the tooth surfaces to be bleached. In other words, if the composition is not applied over substantially the entire interior surface of the barrier layer tray or strip, it is at least applied to that portion of the barrier layer which in use is positioned against the tooth surfaces to be bleached (e.g., at least the labial tooth surface). It is not necessary to apply the bleaching agent destabilizer to regions of the barrier layer which will be positioned against gum tissue during use. In fact it may be preferable in some embodiments to ensure that no bleaching agent destabilizer is present in regions of the barrier layer which will be positioned against gingival tissue so as to prevent reaction with peroxide bleaching agents adjacent the gingival tissue, which may otherwise cause discomfort and soreness. Of course, in embodiments where the destabilizer is compounded within the material of the barrier layer this may be impractical, although discomfort to gingival tissues may be prevented by limiting application of the bleaching composition to regions of the barrier layer corresponding to tooth surfaces to be bleached.

In other words, it may be preferred to apply the bleaching composition so that substantially no bleaching composition is applied adjacent any part of the barrier layer that will be positioned adjacent the gingival tissue, so that the bleaching agent and the destabilizer are only present together at portions of the tray corresponding to tooth surfaces to be bleached. In embodiments where the destabilizer is applied as a film or composition layer, it may be preferable to maintain any portions of the barrier layer which will be positioned adjacent to gingival tissue so that they are substantially free of the bleaching agent destabilizers, and that the destabilizer film or layer is only applied to those portions of the barrier layer corresponding to tooth surfaces to be bleached (e.g., at least the labial tooth surface). In other words, in any embodiment, the bleaching agent and the destabilizer may be present together only at those portions of the tray corresponding to tooth surfaces to be bleached. At portions of the tray that will be positioned adjacent to gingival tissue during use, only one or the other (or neither) of the bleaching agent destabilizer and the bleaching agent are present so as to prevent discomfort and soreness.

In embodiments where the adhesive destabilizer composition is anhydrous, a peroxide bleaching agent may also be included, so long as no water is present so as to prevent premature reaction between the bleaching agent destabilizer and the peroxide bleaching agent. Alternatively, a bleaching composition (e.g., an aqueous gel) may be applied over the layer or film adhesive layer just prior to use. The water within the bleaching composition and/or saliva within the user's mouth causes the bleaching agent destabilizer to be activated in the presence of the bleaching agent.

In another alternative embodiment, a non-custom dental tray or strip according to the invention may be preloaded with a dental bleaching composition. In order to prevent premature contact between the bleaching agent destabilizer and bleaching composition, the tray or strip further includes a protective rupturable membrane disposed between the barrier layer and the bleaching composition. The membrane may be configured to be rupturable subsequent to placement of the tray over the person's teeth. For example, a rupturable membrane of a tray or strip bleaching device may be configured to rupture upon biting, bending and/or folding of the barrier layer and membrane. Such a rupturable membrane may comprise any rupturable layer that is disposed between the bleaching composition and the tray or strip including a bleaching agent destabilizer. Examples of suitable materials include a protective coating layer of high molecular weight polyethylene glycol, a di-para-xylene coating layer, and/or a wax coating. Di-para-xylene is available commercially as Parylene from Parylene Coating Services, Inc., located in Katy, Tex. Such coatings may serve to simply separate the bleaching composition from the barrier layer during storage and shipment, and the coating membrane is ruptured upon biting, bending, and/or flexing of the tray or strip. The rupturable membrane layer may be water-degradable so as to dissolve, degrade, or become dispersed upon contact with moisture (e.g., saliva).

Figure 4:
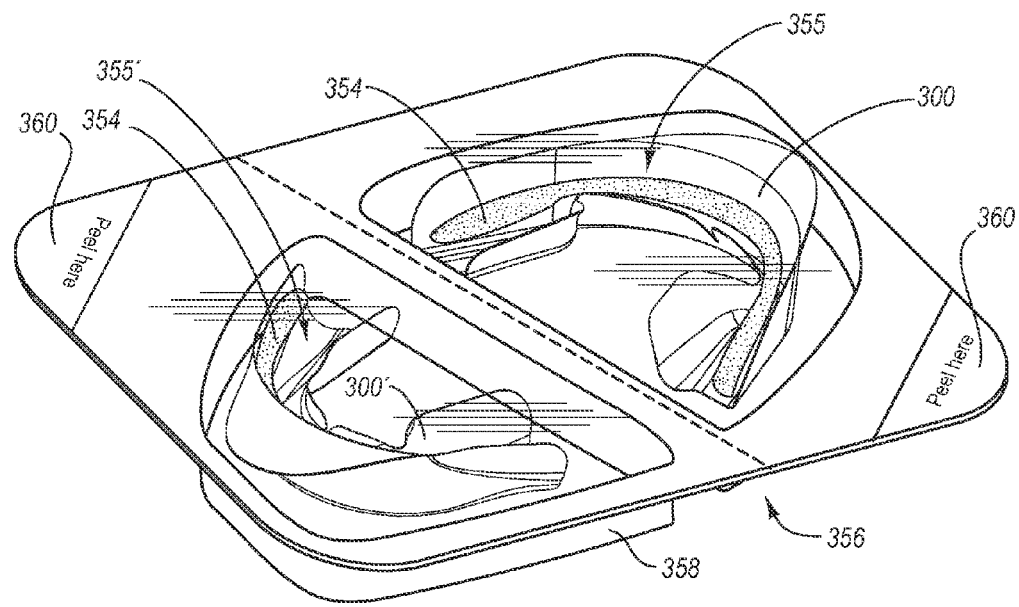
FIG. 4 illustrates a pair of pre-filled tray assemblies similar to the assembly of FIG. 2B contained within a sealed protective package having a peelable cover.

Such a tray or strip may be provided within a sealed container or package to protect the tray or strip, the treatment composition, and rupturable membrane from contaminants and/or premature rupture during storage, transport, and prior to use. FIG. 4 shows a first tray assembly 355 configured for placement over an upper dental arch and a second tray assembly 355' configured for placement over a lower dental arch sealed within protective package 356. Each tray 300 and 300' includes a treatment composition 354 preloaded therein. Protective package 356 includes a rigid support layer 358 and a peelable cover 360. Each tray assembly 355 and 355' may optionally include an additional removable protective layer (not shown) placed adjacent to the treatment composition 354 for additional protection. When it is desired to use the dental treatment tray devices, the peelable cover 360 is removed and the tray assemblies 355 and 355' are removed or separated from support layer 358.

Figure 5:
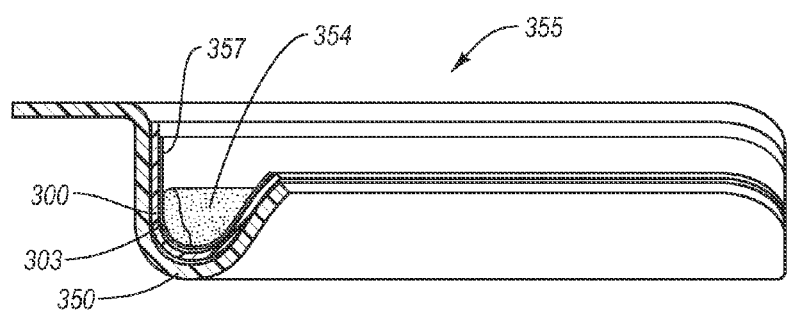
FIG. 5 is a cross-sectional view of a tray assembly including a rupturable membrane between the barrier layer and the treatment composition.

FIG. 5 illustrates a cross-sectional view through tray assembly 355 of FIG. 4, including tray 300 and outer support tray 350, perhaps best illustrating protective rupturable membrane 357 disposed adjacent to inner treatment surface 303 of tray 300.

Another embodiment may include a multi-use tray, for example a custom dental tray formed by vacuum forming a sheet of moisture resistant thermoplastic polymer material over a stone cast of a person's teeth, after which the custom tray may be cut out. Such custom trays can be very comfortable to wear as they provide an excellent fit to the user's dentition. A bleaching agent destabilizer (e.g., a ferric salt) may be compounded with the tray material or otherwise provided so that the bleaching agent destabilizer is present on the interior treatment surface of the tray. During use, the user applies a bleaching composition into the tray, and then places the tray over the teeth for bleaching treatment. The bleaching agent destabilizer, for example, a ferric salt, is oxidized during use so as to form ferrous ions. Because at least some of the bleaching agent destabilizer will likely remain after use, the custom tray may be used multiple times before all the bleaching agent destabilizer has been consumed. Once all bleaching agent destabilizer has been consumed, the custom tray may still be used as a conventional custom bleaching tray, although it will no longer provide the increased bleaching effect afforded by the bleaching agent destabilizer.

The trays and strips may be used with any known dental treatment composition. Examples of treatment compositions include dental bleaching compositions (e.g., including a dental bleaching agent such as a peroxide), desensitizing compositions (e.g., including a desensitizing agent such as potassium nitrate, other potassium salts, citric acid, citrates, and/or sodium fluoride), remineralizing compositions (e.g., including a remineralizing agent such as sodium fluoride, stannous fluoride, sodium monofluorophosphate, and/or other fluoride salts), antimicrobial compositions (e.g., including an antimicrobial agent such as chlorhexidine, troclosan, and/or tetracycline), antiplaque compositions, and anti-tartar compositions (e.g., including an anti-tartar agent such as a pyrophosphate salt). The treatment composition may comprise a sticky viscous gel, a less viscous gel, a highly viscous putty, or a substantially solid composition that is less adhesive prior to being moistened with saliva or water but that becomes more sticky and adhesive when moistened According to one embodiment, the barrier layer comprises a thin (e.g., about 1 mm or less), flexible membrane formed from a polymeric or other moisture-resistant material. Polymeric materials are preferred. In one embodiment, the barrier layer comprises silicone. In another, it comprises ethyl vinyl acetate and polypropylene. According to another embodiment, it may be formed of a polyolefin or similarly moisture-resistant material, such as wax, paraffin, ethylene-vinyl acetate copolymer (EVA), ethylene-vinyl alcohol copolymer (EVAL), polycaprolactone (PCL), polyvinyl chloride (PVC), polyesters, polycarbonates, polyamides, polyurethanes or polyesteramides. Examples of suitable polyolefins for use in making the barrier layer include, but are not limited to, polyethylene (PE), high density polyethylene (HDPE), low density polyethylene (LDPE), ultra low density polyethylene (ULDPE), polypropylene, and polytetrafluoroethylene (PTFE) (e.g., TEFLON). An example of a suitable polyester for use in making the barrier layer includes, but is not limited to, polyethylene terephthalate (PET), an example of which is MYLAR, sold by DuPont. An example of a suitable polyurethane barrier material is a polyurethane film manufactured by ArgoTech, which is located in Greenfield, Mass. The barrier layer may comprise a polymeric blend and/or multiple layers comprising two or more of the foregoing materials. Plasticizers, flow additives, and fillers known in the art can be used as desired to modify the properties of any of the foregoing polymers used to form the barrier layer. The forgoing listing of polymeric materials is not meant to be exhaustive, as numerous other polymeric materials may be used.

Other materials that can act as a barrier layer include metal foil, cellulosic ethers, cellulose acetate, polyvinyl acetate, polyvinyl alcohol, shellac, and chemical or light-cure materials (e.g., methacrylate or acrylate resins). Examples of useful cellulosic ethers that can be used to form a barrier layer include, but are not limited to, ethyl cellulose, propyl cellulose, isopropyl cellulose, butyl cellulose, t-butyl cellulose, and the like. Although non-polymeric moisture resistant materials, e.g., metal foil, may be used, polymeric materials are preferred.

Advantageously, the tray or strip consists essentially of silicone or a silicone like material, as this has been found by the inventors to provide the most beneficial combination of properties, including excellent adaptability, flexibility, softness, and elasticity, while also exhibiting excellent resiliency. Although it is preferred that the moisture resistant polymer material of the tray or strip body consist solely of silicone or one or more silicone like materials, it may be possible in some embodiments to include additional moisture resistant polymer components so that the material comprises a blend of silicone/silicone like materials and other materials. Additional materials that may be included in such an example include one or more elastomers (e.g., a non-silicone like thermoplastic elastomer), latexes, and/or nitriles. Preferably any such additional moisture resistant components comprise no more than about 10% by weight of the tray, more preferably no more than about 5%, and most preferably no more than about 3% by weight. Additional components such as water and/or a plasticizer (e.g., PEG), a colorant, and/or a flavorant may be added to the composition from which the tray or strip body is formed.

Exemplary suitable two-part silicone materials are available from Shin-Etsu Silicones of America, located in Akron, Ohio. One preferred material is KEG2000-50A/B, the physical properties of which are described in the table below. Various other Shin-Etsu silicone products and silicone materials from other suppliers can also be used.

| Property | Value |
| --- | --- |
| Hardness - Shore-A | 52 |
| Tensile Strength - MPa | 11.1 |
| Elongation - % | 580 |
| 100% Modulus - Mpa | 1.72 |
| Tear Strength - kN/m | 40 |
| Comp Set 22 h/302° F. - 1 h/302° F. | 31 |
| Comp Set 22 h/302° F. - 4 h/392° F. | 8 |
| Linear Shrinkage | 2.6 |
| Specific Gravity | 1.13 |
| Viscosity - Part A - Pa · s | 1700 |
| Viscosity - Part B - Pa · s | 1600 |

For example, a silicone material may initially comprise a two-part composition including a first part comprising one or more siloxanes and a second part including an activator. Upon mixing the two liquid parts together, the siloxane molecules polymerize and cross-link so as to form a polysiloxane. Heat may be applied (e.g., by heating the mold) to accelerate polymerization of the silicone material. For example, part A and part B of the raw silicone precursor material are mixed together, which causes the material to begin to polymerize. For many exemplary silicone materials, this reaction could take 2-6 weeks to completely cure at room temperature. Heating the mixture significantly increases the rate at which the material polymerizes. For example, according to one method, the material is heated to 375° F. so as to cause the material to polymerize in a matter of seconds. Actual polymerization time depends on the thickness of the tray or strip being formed. Silicone trays and/or strips may also be formed by other methods, for example with a two part silicone in which polymerization is activated by mixing and/or by compression.

Silicone polymeric materials include a platinum and/or tin catalyst within one or both parts of the composition to assist with polymerization. Advantageously, residual catalyst is present within the material after the tray or strip has been formed. Residual platinum and/or tin catalyst disposed throughout the material, including on the inner treatment surface of the tray or strip, can also act as a bleaching agent destabilizer, acting to produce free radicals from the peroxide bleaching agent upon contact of the barrier layer with a peroxide bleaching composition. Although platinum is a less preferred destabilizer because of its generally higher cost, it is within the scope of the present invention to utilize platinum when present. As the platinum and/or tin may be included in small, silicone-catalyzing amounts (e.g., typically less than 1000 ppm, more typically less than 100 ppm), it may be advantageous to include an additional, more preferred destabilizer, for example magnesium and/or iron in addition to the residual platinum and/or tin, in order to boost the overall destabilizing effect.

Styrene-ethylene-butylene-styrene (SEBS), and/or VERSAFLEX™, a proprietary thermoplastic elastomer alloy exhibiting elasticity and other properties similar to silicone, are examples of silicone-like materials. A suitable example of a SEBS material is SEBS TPE 45A, available from various providers. Physical properties for SEBS TPE 45A are summarized in the table below. Various other SEBS products may also be used in forming a polymeric moisture resistant barrier layer.

| Property | Value |
| --- | --- |
| Density (g/cm$^3$) | 0.94 |
| Surface Hardness - Shore A | 45 |
| Tensile Strength (MPa) | 6 |
| Flexural Modulus (GPa) | 0.02 |
| Notched Izod (kJ/m) | 1.06+ |
| Linear Expansion (/° C. × 10$^{-5}$) | 16 |
| Elongation at Break (%) | 800 |
| Water Absorption (%) | 0.3 |
| Oxygen Index (%) | 19 |
| Melting Temp. Range (° C.) | 200-240 |
| Mold Shrinkage (%) | 1.5 |
| Mold Temp. Range (° C.) | 50-70 |

Several suitable VERSAFLEX™ TPE materials are available from GLS Corporation, located in McHenry, Ill. Preferred VERSAFLEX™ materials include VERSAFLEX™ CL30 and VERSAFLEX™ VERSAFLEX™ CL40, properties of each of which are summarized in the table below. Various other VERSAFLEX™ products from GLS Corporation can also be used.

|  | Product | | |
| Property | CL30 | CL40 | Test Method |
| --- | --- | --- | --- |
| Shore A Hardness, 10 sec delay | 30 | 43 | ASTM D2240 |
| Specific Gravity | 0.89 | 0.89 | ASTM D792, 23/23° C. |
| Tensile Strength | 6619 kPa | 5929 kPa | ASTM D412-Die C, 2 hrs, 23° C. |
| Elongation at Break | 780% | 690% | ASTM D412-Die C, 2 hrs, 23° C. |
| 100% Modulus | 689 kPa | 1379 kPa | ASTM D412-Die C, 2 hrs, 23° C. |
| 300% Modulus | 1448 kPa | 2413 kPa | ASTM D412-Die C, 2 hrs, 23° C. |
| Tear Strength | 19 kN/m | 23 kN/m | ASTM D624 |
| Melt Flow Rate @ 190° C., 2160 g | 18 g/10 min | 13 g/10 min | ASTM D 1238 |
| Melt Flow Rate @ 200° C., 5000 g | 108 g/10 min | 38 g/10 min | ASTM D 1238 |
| Apparent Viscosity @ 200° C. 11170/sec | 15 Pa-s | 16 Pa-s | ASTM D 3835 |
| Compression Set, 22 hrs @ RT | 11% | 12% | ASTM D 395B |

The silicone or silicone like dental trays are characterized by wall thicknesses of no more than about 1 mm, more preferably between about 0.03 mm and about 1 mm, and most preferably between about 0.1 mm and about 0.5 mm. Wall thicknesses greater than about 1 mm are significantly less useful as a comfortable dental bleaching tray, as the thickness of the tray begins to seriously interfere with the normal relaxed position of the occlusal tooth surfaces when wearing such a tray (i.e., the tray(s) get in the way between teeth of opposite dental arches, preventing the user from completely closing their jaw), making the tray significantly less comfortable than a tray with wall thicknesses that are no more than about 1 mm. For this same reason, existing mouth guards formed of silicone have little or no use as a comfortable dental treatment tray as their wall thickness is typically greater than 2 mm, and more typically about 4 mm so as to provide a cushioning effect to the teeth when accepting a blow to the mouth or jaw. Similarly, the inventive dental bleaching trays would be unacceptable for use as a mouth guard, as their thin walls provide little or no protection to the teeth against such blows.

The durometer hardness/softness of the silicone or silicone like tray material is selected so as to strike a balance between softness and wall thickness. Within the preferred wall thicknesses described above (i.e., about 0.03 mm to about 1 mm) the shore A durometer hardness value will preferably range from about 90 to about 20. Generally, higher durometer values (less soft) are preferred with thinner wall trays, while lower durometer values (greater softness) are preferred with thicker wall trays. For example, a tray with a wall thickness of about 0.5 mm may have a shore A durometer hardness value of about 30, a tray with a wall thickness of about 0.25 mm may advantageously have a shore A durometer hardness value of about 40, while a tray with a wall thickness of about 0.1 mm may have a shore A durometer hardness value of about 70. Typical preferred shore A durometer hardness values range from about 30 to about 70, more preferably from about 40 to about 60. In the case of strips, durometer hardness values and preferred thicknesses are similar to the values described above with respect to trays.

The elasticity of the silicone or silicone like tray material is much greater than elasticity of thermoplastic materials (e.g., EVA and/or PP) commonly used in forming trays and strips. For both trays and strips, elasticity (also referred to herein as elongation) of the selected material will preferably range from about 2% to about 2000%, more preferably from about 100% to about 1000%, more preferably from about 300% to about 800%. In addition, elasticity will preferably be no less than about 2%, more preferably no less than about 4%, more preferably no less than about 10%, and most preferably no less than about 25%.

The dental treatment trays according to the invention can be manufactured by injection molding an uncured two-part liquid silicone composition into a mold cavity. In the case of liquid silicone rubber, the two parts are of relatively low viscosity (e.g., 1500-2000 Pa-s), which is significantly lower than the viscosity of thermoplastic materials traditionally used in molding a dental tray or strip. As such, the injection pressures at which the material is injected into the mold are significantly lower (e.g., about 500 to about 5000 psi, typically about 2000 psi) than encountered when injection molding dental trays from EVA, PCL, PVC, and other thermoplastic materials that have been used in injection molding dental trays or strips (e.g., which are typically injected at a pressure of about 20,000 psi). Injection molding with silicone is more easily and inexpensively accomplished relative to the difficulty of molding with more common thermoplastic polymer materials because such trays must be molded with relatively thin walls to achieve an acceptable degree of comfort for the user. For example, plasticizers must be added to increase the melt flow index of the material in order to better fill the entire mold cavity, which is narrow because the manufactured tray must be thin-walled for comfort. It may also be possible to mold the trays from a high consistency silicone material, which is much thicker (e.g., similar to silly putty), and which would require greater manufacturing pressures.

Although it is also possible to form silicone or silicone like dental trays with comparably thin walls (which may have the greatest comfort), this is not always necessary because a silicone or silicone like dental tray of a given thickness exhibits comfort greater than a similarly sized dental tray formed of more common thermoplastic materials (e.g., EVA and PP). As such, a silicone or silicone like tray exhibiting comfort equal to or better than existing trays may have a wall thickness which is significantly greater than the more common thermoplastic tray. In effect, the use of silicone or a silicone like material allows a choice between a relatively thicker wall dental tray which is more easily and inexpensively formed, and which also may not require an outer support tray during placement, or a thin-wall silicone/silicone like dental tray which provides a degree of comfort not found in a comparable tray formed of another material as a result of its thinness, adaptability, flexibility, elasticity, resiliency, and its soft and supple feel.

The dental treatment trays according to the invention can be designed to be worn for any desired time period. Due to the extremely comfortable fit between the inventive dental treatment trays and the person's teeth, it is possible to wear such trays for extended periods of time as desired. The dental treatment trays can be worn for as little as a few minutes or as long as several hours. By way of example, not limitation, a typical treatment session of fast duration may last from about 10 to about 30 minutes; a treatment session of intermediate duration may last from about 30 minutes to about 2 hours; and a treatment session of long duration, including overnight treatment while a person is sleeping, may last from about 2 hours to about 12 hours.

When used in combination with a sticky treatment composition, dental treatment trays may possibly be worn while performing normal daily activities, such as talking, drinking, smoking, coughing, smiling, frowning, grimacing, or while sleeping. Dental treatment trays according to the invention may be worn over a person's upper dental arch, lower dental arch, or both simultaneously. Although trays provide an improved fit as compared to strips that allow treatment as described above, it is of course within the scope of the invention to provide dental treatment strips which can also be used to provide similar treatment. Such strips may be expected to be worn for similar ranges of time as described above, and when used with an initially dry treatment composition that becomes very sticky upon contact with water, may even be worn while engaging in the above described activities as the treatment composition (e.g., a substantially dry treatment composition) more effectively holds the strip in place against the tooth tissues to be bleached.

Figure 6A:
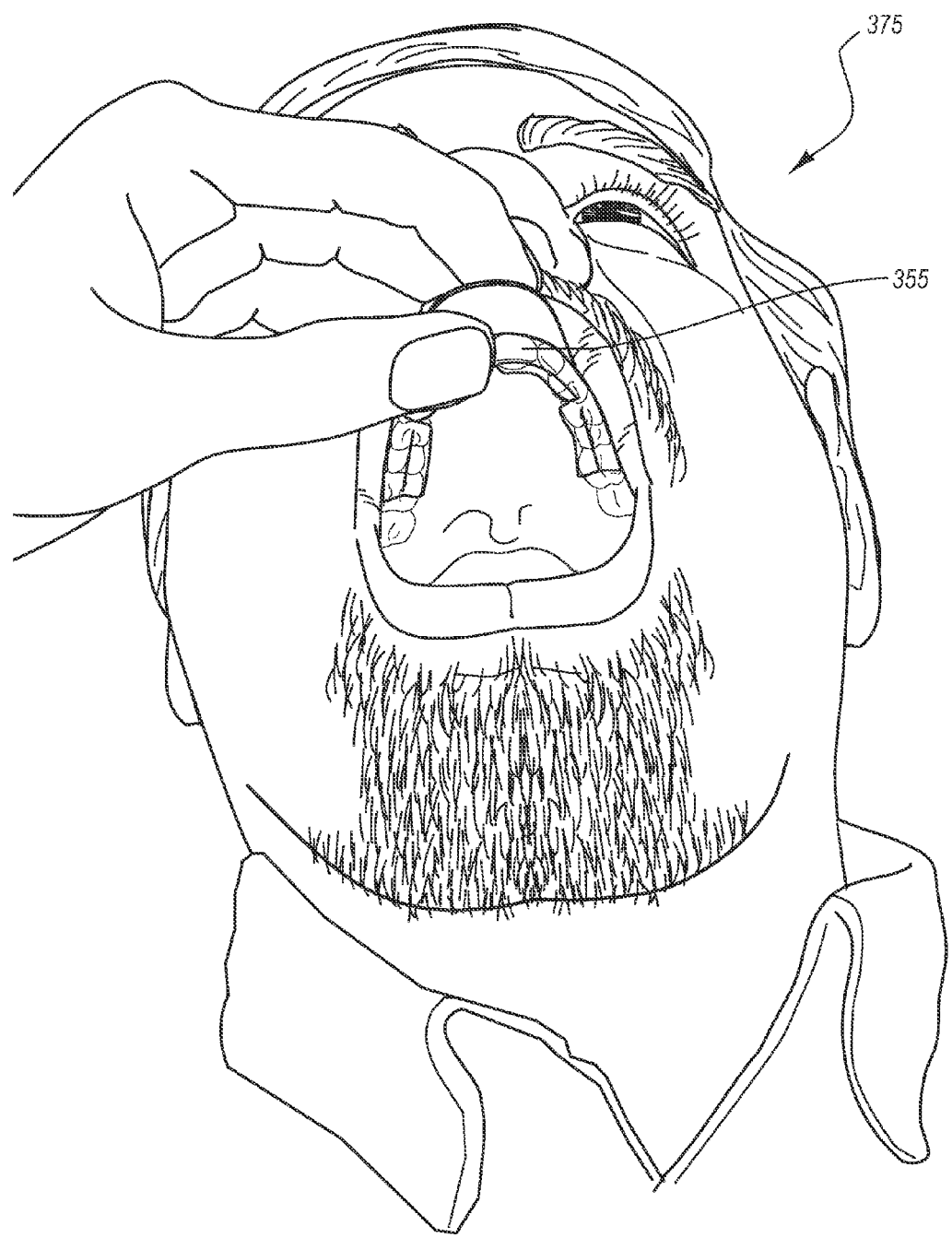
FIG. 6A illustrates a person placing a dental treatment tray according to the invention over the person's upper dental arch.
Figure 6B:
FIG. 6B illustrates dental treatment trays according to the invention in place over both the upper and lower dental arches.

FIG. 6A illustrates a person 375 placing a dental treatment assembly 355 over the person's upper dental arch. The outer support tray helps in placing the inner treatment tray over the teeth. FIG. 6B illustrates a dental treatment tray 300 in place over the person's upper dental arch and a dental treatment tray 300' over the lower dental arch, both outer support trays having been removed.

To remove the dental treatment tray after a desired time period, the user simply grasps a corner or portion of the tray and pulls it off the teeth. Any residual treatment composition that remains adhered to the person's teeth can be removed by washing or flushing with water and/or by brushing.

EXAMPLES OF THE PREFERRED EMBODIMENTS

Following are examples of two-part silicone compositions and alternative silicone like TPE compositions that may be used to manufacture dental treatment trays according to the invention by injection molding. The exemplary formulations and manufacturing conditions are given by way of example, and not by limitation. Unless otherwise indicated, all percentages are by weight.

Example 1

A composition for injection molding a silicone dental treatment tray was formed from Shin-Etsu's KEG2000-50A/B two part thermoset silicone material. Part A containing the activator/hardener had a viscosity of about 1700 Pa-s, while part B containing the siloxane had a viscosity of about 1600 Pa-s. At least one part included a platinum catalyst.

The two parts of the silicone composition were pumped out of storage drums through hoses to a static mixing head where the two parts were mixed together. The mixed silicone material exits the static mixer and was forced into the screw and barrel of the injection molding machine. The mixed silicone material was injected into the heated mold (e.g., about 375° F.), at which point the material quickly polymerized. The tray was removed from the hot mold after polymerization was substantially complete. Exemplary formed trays exhibited excellent adaptability, flexibility, elasticity, and softness, while also being resilient. The molded trays were translucent, had a Shore A durometer hardness of about 50, an elasticity of about 580%. Trays having wall thicknesses of about 0.004 inch (0.10 mm), 0.006 inch (0.15 mm), 0.008 inch (0.2 mm), 0.01 inch (0.25 mm) and 0.014 inch (0.36 mm), respectively, were formed. The trays were found to be very comfortable when worn over a person's dental arch, with better adaptability, flexibility, elasticity, softness, and resiliency as compared to a tray formed of EVA and/or PP. In addition, the silicone material surface exhibited a tendency to adhere (i.e., grip) to tooth surfaces.

It is believed that the residual platinum catalyst content within the finished tray was less than 1000 ppm, more likely less than 100 ppm. The presence of residual platinum catalyst within the silicone material provided available platinum ions to act as a bleaching agent destabilizer when contacted with a peroxide dental bleaching agent.

Example 2

A composition for injection molding a dental treatment tray was formed from SEBS TPE 45A material. The heated material was pumped so as to be forced into the screw and barrel of the injection molding machine. The material was injected into the mold. The cooled tray was removed from the mold. Exemplary formed SEBS trays exhibited excellent adaptability, flexibility, elasticity, and softness, while also being resilient, similar to the silicone tray of Example 1. The molded trays were translucent, had a Shore A durometer hardness of about 45, an elasticity of about 800% and a wall thickness of about 0.020 inch (0.5 mm). The trays were found to be very comfortable when worn over a person's dental arch, with better adaptability, flexibility, elasticity, softness, and resiliency as compared to a tray formed of EVA and/or PP. In addition, the SEBS material surface exhibited a tendency to adhere (i.e., grip) to tooth surfaces. A bleaching agent destabilizer (e.g., about 0.1 percent to about 5 percent by weight) may be compounded with the SEBS material prior to molding so that the finished trays include the bleaching agent destabilizer on the inner surface of the tray.

Example 3

A composition for injection molding a dental treatment tray is formed from VERSAFLEX™ CL30. The heated TPE material is pumped so as to be forced into the screw and barrel of the injection molding machine. The material is injected into the mold. The cooled tray is removed from the mold. Exemplary formed VERSAFLEX™ CL30 trays exhibit excellent adaptability, flexibility, elasticity, and softness, while also being resilient, similar to the silicone tray of Example 1. The molded trays are translucent, have a Shore A durometer hardness of about 30, an elasticity of about 780% and a wall thickness of about 0.020 inch (0.5 mm). The trays are very comfortable when worn over a person's dental arch, with excellent adaptability, flexibility, elasticity, softness, and resiliency as compared to a tray formed of EVA and/or PP. In addition, the VERSAFLEX™ CL30 material surface exhibits a tendency to adhere (i.e., grip) to tooth surfaces. A bleaching agent destabilizer (e.g., about 0.1 percent to about 5 percent by weight) may be compounded with the VERSAFLEX™ material prior to molding so that the finished trays include the bleaching agent destabilizer on the inner surface of the tray.

Example 4

A composition for injection molding a dental treatment tray is formed from VERSAFLEX™ CL40. The heated TPE material is pumped so as to be forced into the screw and barrel of the injection molding machine. The material is injected into the mold. The cooled tray is removed from the mold. Exemplary formed VERSAFLEX™ CL40 trays exhibit excellent adaptability, flexibility, elasticity, and softness, while also being resilient, similar to the silicone tray of Example 1. The molded trays are translucent, have a Shore A durometer hardness of about 40, an elasticity of about 690% and a wall thickness of about 0.020 inch (0.5 mm). The trays are very comfortable when worn over a person's dental arch, with excellent adaptability, flexibility, elasticity, softness, and resiliency as compared to a tray formed of EVA and/or PP. In addition, the VERSAFLEX™ CL40 material surface exhibits a tendency to adhere (i.e., grip) to tooth surfaces. A bleaching agent destabilizer (e.g., about 0.1 percent to about 5 percent by weight) may be compounded with the VERSAFLEX™ material prior to molding so that the finished trays include the bleaching agent destabilizer on the inner surface of the tray.

Following are examples of dental treatment compositions that can be used in combination with silicone or silicone like dental treatment trays or strips of the invention.

Example 5

An initially flowable composition suitable for use in manufacturing a substantially solid treatment composition was formed by mixing together the following components:

| | |
|---|---|
| Ethanol | 31.95% |
| Water | 10% |
| Polyvinyl Pyrrolidone (M.W. = 1.3 million) | 27% |
| Polyvinyl Pyrrolidone (M.W. of about 60,000) | 10% |
| Sodium Laurel Sulfate | 0.5% |
| Glycerine | 15% |
| Sucralose 25% solution | 0.5% |
| Peach Flavor | 4% |
| Potassium Nitrate | 0.8% |
| Sodium Fluoride | 0.25% |

The resulting composition is spread over the surface of a pre-molded silicone or silicone like dental tray or strip and then dried so as to form a substantially solid treatment composition. The treatment composition is initially dry to the touch, but became very sticky when contacted with water or saliva during use. The potassium nitrate provides a dental desensitizing effect. The sodium fluoride provides both a desensitizing and remineralizing effect. The trays and strips reliably adhere to tooth tissue, and exhibit excellent comfort and adhesiveness.

Example 6

A sticky, viscous dental bleaching composition was prepared by mixing together the following components:

| | |
|---|---|
| Water | 22.5% |
| EDTA Disodium | 0.1% |

-continued

| | |
|---|---|
| Carbamide Peroxide | 18.5% |
| Sucralose 25% solution | 0.75% |
| Glycerine | 41.6% |
| Carbopol 974 | 5.3% |
| Sodium Hydroxide 50% solution | 2.25% |
| Polyvinyl Pyrrolidone (M.W. = 1.3 million) | 2% |
| Carboxymethyl Cellulose | 4% |
| Watermelon Flavor | 3% |

All fractions are by weight. A bite ruptureable membrane is positioned adjacent the inner treatment surface of a tray shaped or strip shaped barrier layer. A bead of dental bleaching composition is then spread along the ruptureable barrier layer adjacent the dental bleaching tray. The bleaching composition may be positioned adjacent the labial-buccal wall of the tray, as illustrated in FIG. 5. In the case of a strip, the dental bleaching composition is applied evenly over one side of the strip shaped barrier layer, with the rupturable membrane between the composition and the barrier layer. During placement and/or use the rupturable membrane is broken, contacting the composition to the barrier layer. Upon contact of the bleaching composition with the barrier layer, the peroxide dental bleaching agent is destabilized so as to accelerate production of free radicals. The trays and strips reliably adhere to tooth tissue, and exhibit excellent comfort and adhesiveness.

Additional exemplary dental treatment compositions, and methods for making such compositions, which may be used with devices according to the invention are disclosed in U.S. Pat. No. 5,376,006; U.S. Pat. No. 5,785,527; U.S. Pat. No. 5,851,512; U.S. Pat. No. 5,858,332; U.S. Pat. No. 5,985,249; U.S. Pat. No. 6,306,370; U.S. Pat. No. 6,309,625; U.S. Pat. No. 6,312,671; U.S. Pat. No. 6,322,774; U.S. Pat. No. 6,368,576; U.S. Pat. No. 6,387,353; U.S. Pat. No. 6,500,408; U.S. Pat. No. 6,503,485 and U.S. patent application Ser. No. 11/460,016 filed Jul. 26, 2006. For purposes of disclosing dental treatment compositions, and methods of making such compositions, the foregoing patents and application are incorporated herein by reference.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A non-customized dental treatment tray for use in applying a dental treatment composition to a person's teeth and/or gums and which is highly adaptable in order to approximate the comfort and fit of a customized dental tray, comprising:

a non-customized barrier layer formed from a moisture-resistant elastomeric material in the shape of a dental tray, wherein the non-customized barrier layer is devoid of structures corresponding to a size and shape of a person's unique dentition so as to comfortably fit over a plurality of differently-sized and shaped teeth and dental arches corresponding to different people, wherein the elastomeric material consists essentially of a non-silicone, silicone-like thermoplastic elastomer having a Shore A hardness of 45 or below, wherein the non-customized barrier layer is soft, flexible and elastically deformable in order to be highly adaptable so that, when placed over a person's teeth during use, the non-customized barrier layer adapts and at least partially conforms to unique ridges, depressions and contours of the person's teeth.

2. A non-customized dental treatment tray as in claim 1, wherein the non-silicone, silicone-like thermoplastic elastomer comprises styrene-ethylene-butylene-styrene thermoplastic elastomer.

3. A non-customized dental treatment tray as in claim 1, wherein the non-silicone, silicone-like thermoplastic elastomer is a thermoplastic elastomer alloy.

4. A non-customized dental treatment tray as in claim 3, wherein the thermoplastic elastomer alloy has a shore A hardness of 43 or below.

5. A non-customized dental treatment tray as in claim 1, wherein the non-customized barrier layer has a thickness of less than about 1.5 mm.

6. A non-customized dental treatment tray as in claim 1, wherein the non-customized barrier layer has a thickness of less than about 1 mm.

7. A non-customized dental treatment tray as in claim 1, wherein the non-customized barrier layer has a thickness of less than about 0.5 mm.

8. A non-customized dental treatment tray as in claim 1, wherein the moisture-resistant elastomeric material of the barrier layer is blended with at least one auxiliary component selected from the group consisting of elastomers, latexes, water, plasticizers, and nitriles.

9. A non-customized dental treatment tray as in claim 1, wherein the moisture-resistant elastomeric material has an elasticity between about 2% and about 2000%.

10. A non-customized dental treatment tray as in claim 1, wherein the moisture-resistant elastomeric material has an elasticity between about 100% and about 1000%.

11. A non-customized dental treatment tray as in claim 1, wherein the elastomeric material further includes more than 0% and up to about 10% by weight of an auxiliary component.

* * * * *